US012514761B2

(12) United States Patent
Högberg et al.

(10) Patent No.: US 12,514,761 B2

(45) Date of Patent: Jan. 6, 2026

(54) WASHABLE SANITARY PRODUCT

(71) Applicant: AB Lindex, Gothenburg (SE)

(72) Inventors: Karin Högberg, Mölnlycke (SE); Lena Berglin, Gothenburg (SE)

(73) Assignee: AB Lindex, Gothenburg (SE)

( * ) Notice: Subject to any disclaimer, the term of this patent is extended or adjusted under 35 U.S.C. 154(b) by 516 days.

(21) Appl. No.: 17/923,706

(22) PCT Filed: May 7, 2021

(86) PCT No.: PCT/EP2021/062207

§ 371 (c)(1),
(2) Date: Nov. 7, 2022

(87) PCT Pub. No.: WO2021/224482

PCT Pub. Date: Nov. 11, 2021

(65) Prior Publication Data

US 2023/0201048 A1 Jun. 29, 2023

(30) Foreign Application Priority Data

May 7, 2020 (EP) .................................... 20173453

(51) Int. Cl.

*A61F 13/15* (2006.01)
*A61F 13/475* (2006.01)

(Continued)

(52) U.S. Cl.

CPC ........ *A61F 13/4753* (2013.01); *A61F 13/514* (2013.01); *A61F 13/537* (2013.01); (Continued)

(58) Field of Classification Search

CPC .. A61F 13/4753; A61F 13/514; A61F 13/537; A61F 13/15268; A61F 2013/15276; A61F 2013/53445

See application file for complete search history.

(56) References Cited

U.S. PATENT DOCUMENTS 6,103,641 A * 8/2000 Gehring, Jr. ........... D04B 21/16 428/911

7,015,370 B2 * 3/2006 Watanabe ............. A61F 13/512 604/385.101

(Continued)

FOREIGN PATENT DOCUMENTS

CN 110742733 A 2/2020

EP 0565630 A1 10/1993

(Continued)

OTHER PUBLICATIONS

International Preliminary Report on Patentability for Application No. PCT/EP2021/062207, dated Nov. 8, 2022, 8 pages.

(Continued)

*Primary Examiner* — Jacqueline F Stephens

(74) *Attorney, Agent, or Firm* — Noréns Patentbyrå AB

(57) ABSTRACT

The present inventive concept relates to a washable sanitary product. The sanitary product comprises a liquid impermeable back sheet, a liquid retaining pad, having an outer surface area adapted to reside nearest the skin of the user and an inner surface resting against the back sheet, wherein a peripheral portion of said back sheet extends radially outside a perimeter of said liquid retaining pad. The sanitary product further comprises a liquid impermeable annular liner being sealingly attached to the outer surface of the liquid retaining pad along the peripheral portion of the liquid retaining pad by a first seal and to the peripheral portion of the back sheet by a second seal, such that the peripheral portion of the liquid retaining pad is sandwiched between the back sheet and the liner. The annular liner and the back sheet together form a liquid impermeable container for said liquid retaining pad. The liquid retaining pad comprises least one element of spacer fabric that serves as both liquid distribution layer and as liquid retaining layer.

15 Claims, 5 Drawing Sheets

(51) Int. Cl.
*A61F 13/514* (2006.01)
*A61F 13/537* (2006.01)
*A61F 13/534* (2006.01)

(52) U.S. Cl.
CPC ............... *A61F 2013/15276* (2013.01); *A61F 2013/53445* (2013.01)

(56) References Cited

U.S. PATENT DOCUMENTS

| | | | |
|---|---|---|---|
| 7,090,666 B2 | 8/2006 | Miskie | |
| 7,361,803 B2 * | 4/2008 | Miskie | A61F 13/505 604/378 |
| 2006/0100597 A1 | 5/2006 | Miskie | |
| 2010/0152692 A1 | 6/2010 | Ong et al. | |
| 2018/0014983 A1 | 1/2018 | Jayasuriya et al. | |

FOREIGN PATENT DOCUMENTS

| | | | |
|---|---|---|---|
| EP | 2992864 | A1 | 3/2016 |
| EP | 3437604 | A1 | 2/2019 |
| EP | 4147869 | A1 | 3/2023 |
| WO | 2005051656 | A1 | 6/2005 |
| WO | 2007073506 | A2 | 6/2007 |
| WO | 2014101928 | A1 | 7/2014 |
| WO | 2014102072 | A1 | 7/2014 |
| WO | 2015012155 | A1 | 1/2015 |
| WO | 2021224482 | A1 | 11/2021 |

OTHER PUBLICATIONS

PCT International Search Report and Written Opinion completed by the ISA/EP on Jul. 23, 2021 and issued in connection with PCT/EP2021/062207.

* cited by examiner

WASHABLE SANITARY PRODUCT

CROSS-REFERENCE TO RELATED APPLICATIONS

This application is a U.S. national counterpart application of International Application Serial No. PCT/EP2021/062207, filed May 7, 2021, which claims priority to and the benefit of European Patent Application No. 20173453.0, filed May 7, 2020, the contents of each which is incorporated by reference herein in their entireties.

TECHNICAL FIELD OF THE INVENTION

The present inventive concept relates to a washable sanitary product, and more particularly, to a washable sanitary product comprising a spacer fabric.

BACKGROUND OF THE INVENTION

Washable and reusable sanitary products have been used during centuries among men and women around the world and are still commonly used by people in the third world countries. For many women it is a problem to socialize with other people during the period of menstruation due to lack of sufficient sanitary protection.

Similar to consumable sanitary products, it is of great importance that reusable sanitary products have an absorbent capacity that fulfills the requirements of minimal leakage and a sense of dryness to the user. However, reusable sanitary products must also be possible to thoroughly wash and to dry in a reasonable amount of time. These criteria are often contradictory, and the outcome is either a sanitary product which is easy to dry but does not absorb a large volume of liquid or a sanitary product that takes a long time to dry but has good absorption capacity.

The basic model for an absorbable sanitary product could be described as a multilayer structure consisting of three layers. The first layer, the top sheet/acquisition layer which is in direct contact with the body allows the fluid to enter the absorbent product quickly. The next layer serves to spread and distribute the fluid over a large area so that the capacity of the pad to absorb and hold fluid could be maximized. The third layer, the absorbent core makes the fluid immobile within the structure and hold without releasing the fluid under normal pressure.

In U.S. Pat. No. 7,090,666 there is described a launderable and reusable moisture management incontinence pad that is free from overlying moisture barriers and that is easy to wash and dry. The incontinence pad comprises a multi-layer fabric composite that comprises a plurality of overlying absorbent layers. The absorbent layers are substantially unattached to one another along respective first and second longitudinal side edges to promote circulation between the layers during laundering and to promote fast drying. However, the use of absorbent layers nearest the skin without a overlying moisture barrier makes the incontinence pad feel wet during use and still takes long time to wash and dry since it comprises absorbing materials.

To solve the problem of not having an absorbent layer nearest the skin of the user spacer fabrics may be used in sanitary products as a liquid distribution layer to be placed nearest the skin of the user. A spacer fabric is a three-dimensional fabric that comprises a first layer that is connected to a second layer by intermediate threads.

In WO 2005/051656 there is disclosed a multi-layer moisture management fabric composite. The fabric comprises a three-dimensional fabric spacer adapted for residing nearest the skin, a plurality of overlying moisture-absorbent layers residing outside of the spacer, and a liquid impermeable jacket residing outside of the absorbent layers. The fabric is constructed to be washable, reusable and retain its qualities after repeated washings. The purpose of the fabric spacer is to distribute and lead the liquid to the underlying absorbing layers. The reason for using a spacer fabric in combination with absorbing layers is that the spacer fabric which is located nearest the skin of the user promotes a sense of dryness to the user during use and helps to guide the liquid to the underlying absorbing layers. However, the presence of absorbing layers in the fabric promotes difficulties to wash and long time for drying when washed.

Document WO2014/102072 describes a liquid distribution layer for disposable incontinence products. The liquid distribution layer is a spacer fabric that comprises a first flat knitted layer, a second flat knitted layer having a pattern of openings 28, and spacer threads which connects the first knitted layer and the second knitted layer to each other. The advantage of having a spacer fabric as a liquid distribution layer is to achieve good compression hardness with a low basis weight. Another advantage according to WO2014102072 is that with the preferred use of super absorbent polymers in an adjacent absorbent layer, liquid distribution over a larger area is necessary, because otherwise local swellings can occur.

Incontinence products in general require higher absorbing capacity than sanitary products for women since the viscosity of urine is much lower than the viscosity of menstrual blood. The presence of absorbing materials is therefore important in incontinence products. On the other hand, absorbing materials make a sanitary product more difficult, or even unsuitable, for wash and dry, and is consequently not suitable in washable sanitary products.

The present inventive concept seeks to provide a washable sanitary product which is less complex and easier to wash and dry for reuse. The present inventive concept also seeks to provide a washable sanitary product which is less expensive than prior art solutions.

SUMMARY OF THE INVENTION

An object of the inventive concept is to mitigate the above problems, and to provide a washable sanitary product which can be washed and dried more efficiently, with maintained liquid retaining performance. A further object is to provide such a sanitary product which is less complex, and thus more cost efficient, than prior art solutions. These, and other objects which will become apparent in the following, are accomplished by means of a washable sanitary product as defined in the accompanying claims.

According to a first aspect of the invention, the above objects are achieved by a washable sanitary product comprising a liquid impermeable back sheet and a liquid retaining pad, having an outer surface area adapted to reside nearest the skin of the user and an inner surface resting against the back sheet, wherein a peripheral portion of the back sheet extends radially outside a perimeter of the liquid retaining pad. The sanitary product further comprising a liquid impermeable annular liner being sealingly attached to the outer surface of the liquid retaining pad along the peripheral portion of the liquid retaining pad by a first seal and to the peripheral portion of the back sheet by a second seal, such that the peripheral portion of the liquid retaining pad is sandwiched between the back sheet and the liner, wherein the annular liner and the back sheet together form a liquid impermeable container for the liquid retaining pad, wherein the liquid retaining pad comprises at least one element of spacer fabric that serves as both liquid distribution layer and as liquid retaining layer.

As mentioned, above, a spacer fabric is a three-dimensional fabric that comprises a first layer that is connected to a second layer by intermediate spacer yarns. The present inventive concept is based on the surprising insight that a layer of such a spacer fabric surrounded by a liquid impermeable container will provide sufficient liquid retaining performance, especially for liquids with sufficiently high viscosity, e.g. blood, such that the need of absorbing materials may be reduced or completely avoided. Moreover, the spacer yarns ensure that the spacer fabric can sustain compression to some extent, and thus retain the liquid also when the sanitary product is subject to pressure. The flexible container formed by the back sheet and annular liner ensures that the liquid retaining pad is even further protected from leakage; especially at the edges of the liquid retaining pad.

Preferably, the spacer fabric is a textile composite based on hydrophobic knitted spacer with the ability to penetrate, distribute and retain smaller as well as larger amount of menstruation blood using capillary absorption (quick penetration, distribution, absorption and retention of liquid at the different layers of the spacer structure).

In prior art solutions, such as WO2014/102072 mentioned above, a spacer fabric is sometimes used as a distribution layer but not for liquid retention. Consequently, prior art solutions always require additional liquid absorbing layers. According to the present invention, the spacer fabric is used both for liquid distribution and liquid retaining. By having less (or no) absorbing layers in the sanitary product, the time required for washing and drying may be significantly reduced.

The sanitary product is also, with regards to its simplicity, cheap to produce which is a great benefit for women in the third world countries.

According to at least one example embodiment, the spacer fabric is a three-dimensional fabric made of an upper layer, a lower layer, and an interconnecting layer of pile filaments that serve as spacer yarns.

One example of a warp-knitted spacer fabric is disclosed in WO2014/101928 herewith incorporated by reference. Another possibility is to have a non-woven spacer fabric.

The inventors have found that when a liquid such as blood enters such a spacer fabric it is partly spread in the upper layer and partly guided by the spacer yarns down to the lower layer. The spreading is caused by capillary action (sometimes referred to as wicking or capillary absorption). In the case of warp-knitted fabric, the capillary action takes place primarily in the mesh direction of the upper and lower layers, but also somewhat in the counter mesh direction. Since the liquid is spread in three interconnected layers, by wicking, the spacer fabric can take up and hose a large volume of liquid. (The liquid retention is also due to the compression resistance of the interconnecting layer. The interconnecting layer contributes to the retention of liquid.)

The spreading of liquid will be dependent on the flow resistance of a layer. A layer with higher flow resistance will spread liquid more than a layer with lower flow resistance. Therefore, it is beneficial that the upper layer (closest to the user) has a lower flow resistance than the lower layer.

In a warp-knitted fabric, a lower flow resistance can be accomplished with less dense mesh, i.e. a mesh with larger mesh openings.

With this design, the spreading of liquid is greater in the lower layer than in the upper layer. Thus, the liquid passes more quickly through the upper layer (closest to the user) which is beneficial since the surface of the sanitary product will feel drier. The upper layer of the spacer fabric thus serves as a penetration layer, ensuring that liquid (e.g. blood) will quickly enter the liquid retaining pad and ensure satisfactory user comfort.

The spreading of liquid will also be dependent on the mesh direction of the layer. According to at least one example embodiment, a mesh direction of the upper layer and lower layer are in the length direction of the sanitary product. Hereby, the mesh direction of the upper and lower layers is the same. This means that the liquid entering the spacer fabric is, thanks to the upper and lower layers, mainly spread in the length direction of the sanitary product while the spacer yarns spreads the liquid downwards.

In one example embodiment, the spacer fabric element is located on the back sheet without any intermediate liquid absorbing materials.

This should be understood as the spacer fabric being located on the back sheet without any intermediate liquid retaining layers. Liquid absorbing materials is in this context meant to include moisture absorbing materials, such as moisture absorbent fibers. A moisture absorbent fiber is defined as a fiber which swells more than 20% when wet. Absorption of liquid into a porous structure can occur by two different processes. In the first process the liquid enters the porous structures due to intermolecular bonding of water molecules in the chemical composition and swelling of the structures where the liquid is further diffused into the structure. The second process, capillary absorption or wicking, liquid is absorbed into the structures by capillary forces into spaces and pores within the structure.

Hydrophilic materials are good absorbers but while absorbing liquid they collapse and their ability to retain fluid decreases due to the poor compression resistance of the material. Synthetic fibers such as polyester have excellent resilience together with high compression resistance in wet conditions. The interconnective layer in the spacer fabrics, also play an important role for the retention of liquid.

Non-limiting examples of moisture absorbent fibers are natural or regenerated fibers; such as cotton, wool, viscose, bamboo or hemp. These fibers have in common that they are hydrophilic, i.e. have an affinity to water. If a droplet spreads, wetting a large area of the surface of a fabric, and the contact angle is less than 90 degrees, that surface of the fabric is considered hydrophilic.

Most synthetic fibers, on the contrary, possess hydrophobic properties. When a droplet of liquid is in contact with the surface of a hydrophobic fiber, the droplet is not spread as much as for a hydrophilic fiber. Also, the liquid is not absorbed into a hydrophobic fiber as much as for a hydrophilic fiber. This is related to the absorption capacity of the fiber, defined as the amount of liquid a solid material can absorb. Absorbing fibers, that possess high absorption capacity, would negatively affect the time to get the sanitary product dry. Furthermore, the more liquid absorbed into the fiber, the more thorough wash is required to get the fiber clean again. This is related to both longer time for wash and more water required during the wash.

When hydrophilic materials absorb liquid, they collapse and their ability to retain fluid decreases dur to the poor compression resistance of the material. Synthetic materials have excellent compression resistance together with good resilience also in wet conditions which improves their ability to retain fluid.

In its most primitive form, the liquid retaining pad may be formed by a single element of spacer fabric. Preferably, however, the liquid retaining pad comprises an outer spacer fabric element, intended to be facing the skin of a user and at least one intermediate spacer fabric element sandwiched between the outer spacer fabric element and the back sheet.

By having more than one element of spacer fabric in the liquid retaining pad, the absorption capacity of the liquid retaining pad can be further increased. The sanitary product can be ensured to be washable and dryable in a satisfactory amount of time also when it is made of several elements.

In the case of several spacer fabric elements, at least one intermediate spacer fabric element may have a smaller surface area than the surface area of the outer spacer fabric element and be located such that the outer spacer fabric covers the at least one intermediate spacer fabric element.

Hereby, the outer spacer fabric element completely covers the underlying intermediate space fabric element and extends radially outside the perimeter of the intermediate spacer fabric element. This design has benefits during manufacture, as the annular liner more easily can be attached to the back sheet. Also, the liquid retaining pad can be manufactured such that it has higher absorption capacity in the middle of the liquid retaining pad. Moreover, the liquid retaining pad is thus thinner in the edge of the liquid retaining pad providing for good ergonomics of the sanitary product.

It should be understood that the perimeter of the liquid retaining pad may include only the outer spacer fabric in circumstances where the liquid retaining pad consists of more than one element of spacer fabric. Hereby, not the entire thickness of the liquid retaining pad is included in the periphery of the liquid retaining pad.

In one example embodiment, the annular liner and/or the back sheet is made of thermoplastic material such as polyesters, polyamides, polyolefines or combinations thereof. These kinds of materials are all liquid impermeable and provides for an annular liner with flexible properties. Furthermore, none of these materials possess high absorption capacity and thus not count as liquid absorbing materials. They also have good compression resistance improving the retention capacity. The annular liner is preferably made of the same material as the back sheet. This makes the sanitary product having limited amount of different materials, easy to produce, and less expensive.

According to a second aspect of the present inventive concept, the above objects are achieved by a method to produce a washable sanitary product, the method comprises providing a spacer fabric element, sealingly attaching a liquid impermeable annular liner to a peripheral portion of the spacer fabric element such that a radially extending portion of the annular liner extends radially outside the perimeter, sealingly attaching the radially extending portion to a liquid impermeable back sheet, such that the perimeter of the spacer fabric element is sandwiched between the back sheet and the liner, wherein the annular liner and the back sheet together form a liquid impermeable container for the spacer fabric element.

The advantages described above relating to the invention according to the first aspect applies as well on the invention according to the second aspect.

The annular liner may be attached to the spacer fabric element and to the back sheet by means of heat lamination. Heat lamination is a simple and fast way to provide an adhesive layer to a substrate. It is done by means of pressure and heat and can be applied on for example standard thermal laminating films, Low-temperature thermal laminating films, Heat set (or heat-assisted) laminating films or Pressure-sensitive films.

According to at least one example embodiment, the spacer fabric element is an outer spacer fabric element and the method further comprises providing an inner spacer fabric element, attaching the inner spacer fabric element to the back sheet before the step of sealingly attaching the radially extending portion of the annular liner to the back sheet. In case of several spacer fabrics elements, it is preferable that a spacer fabric element residing closest to the back sheet is attached to the back sheet. This simplifies the production of the sanitary product.

When the inner spacer fabric element is attached to the back sheet, e.g. by heat lamination, it may be slightly compressed. Therefore, it may be advantageous that the inner spacer fabric element is thicker—e.g. a few mm ticker—than the outer spacer fabric element and/or the at least one intermediate spacer fabric element. Thereby, all spacer fabric elements of the manufactured product may have substantially the same thickness.

BRIEF DESCRIPTION OF THE DRAWINGS

The inventive concept, some non-limiting embodiments, and further advantages of the inventive concept will now be described with reference to the drawings in which.

DETAILED DESCRIPTION OF THE DRAWINGS

In the following description, the present inventive concept is described with reference to a washable sanitary product 100.

Figure 1A:
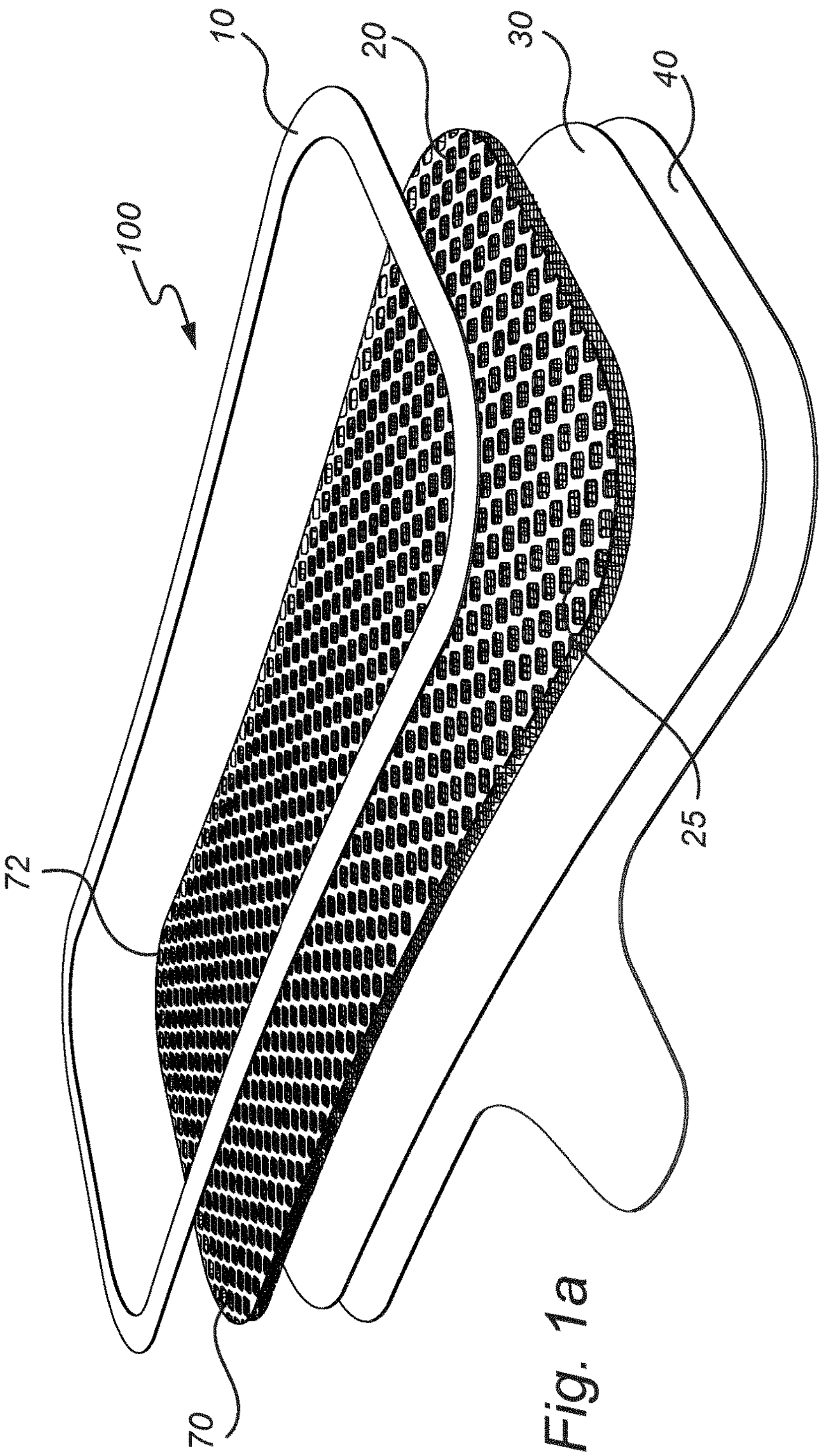
FIG. 1*a* illustrates, in an exploded view, a washable sanitary product according to a first embodiment of the invention, having a single spacer fabric element.
Figure 1B:
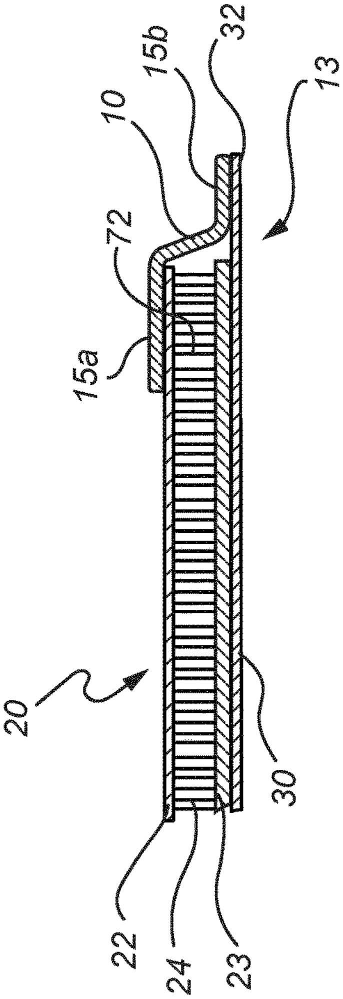
FIG. 1*b* is a cross section of the sanitary product of FIG. 1*a*.

FIG. 1*a-b* illustrate a sanitary product 100 that is made of an annular liner 10, a liquid retaining pad 70, and a back sheet 30 (counting from the upper part of the sanitary product 100). The sanitary product 100 of FIG. 1*a* additionally has an underlying layer 40 that is meant to adhere to an undergarment.

The liquid retaining pad 70 is located on top of the back sheet 30. The back sheet 30 is liquid impermeable and covers the entire lower layer of the spacer fabric in the retaining pad 70 such that it makes the underside of the sanitary product 100 liquid impermeable. Preferably, the back sheet 30 is flexible such that it promotes comfort to the user. It can for example be made of an adhesive film comprising thermoplastic materials such as polyolefines, polyesters, polyamides or combinations thereof. The back sheet 30 is, as illustrated in FIG. 1*a*, typically attached to an underlying layer 40 that is meant to adhere to an undergarment. However, it can also be attached directly to an undergarment without any underlaying layer (see FIG. 5).

As illustrated in FIG. 1*b*, the back sheet 30 extends radially outside a peripheral portion 72 of the liquid retaining pad 70. This extending portion 32 of the back sheet 30 is sealed to the annular liner 10. Similar to the back sheet 30, the annular liner 10 is preferably made of an adhesive material as described above, such that it adapts to the user. The annular liner 10 is preferably made of the same material as that of the back sheet 30.

As illustrated in FIG. 1*b*, the annular liner 10 is attached to an upper side of a peripheral portion 72 of the liquid retaining pad 70 along a first seal 15*a*. Further, the annular liner 10 is attached to a peripheral portion 32 of the back sheet 30 along a second a seal 15*b*. In the illustrated example, the first seal 15*a* is 3-5 mm wide, while the second seal 15*b* is 2-4 mm wide.

Hereby, the peripheral portion 72 of the liquid retaining pad 70 is sandwiched between the back sheet 30 and the annular liner 10 such that the back sheet 30 and the annular liner 10 together form a sealed flexible container 13 for the liquid retaining pad 70. It is important that the seals 15*a*, 15*b* extend along the entire peripheral portion 72 of the liquid retaining pad 70 in order to prevent any liquid held inside the pad 70 from leaking out at the edges.

The seals 15*a*, 15*b* also protect the liquid retaining pad 70 from tearing during laundering. The sealed flexible container 13 thus has two functions; it prevents the liquid kept inside the liquid retaining pad 70 from leaking out and it protects the liquid retaining pad 70 from tearing during laundering.

The liquid retaining pad 70 includes at least one element of spacer fabric, and in the example in FIG. 1*a* it includes only one spacer fabric element 20. A spacer fabric is understood as a three-dimensional fabric that comprises a first, upper layer 22 that is connected to a second, lower layer 23 by an intermediate spacer layer 24. The spacer fabric element 20 has a thickness sufficient to provide the required liquid retaining capacity, and may for example be in the range 2-10 mm, typically in the range 3-5 mm. As a specific example, the spacer fabric element in the illustrated embodiment may be 3 mm, 4 mm or 5 mm thick.

An example of a commercially available spacer fabric is disclosed in WO2014/101928, hereby incorporated by reference, in which case the spacer fabric is warp knitted.

The upper and lower layers 22, 23 here have openings 25 to improve liquid permeability. The openings of the lower layer are preferably smaller than the openings of the upper layer, such that the lower layer 26 is denser and has higher flow resistance than the upper layer 22. Because of this, the liquid kept inside the liquid retaining pad 70 is spread more in the lower layer 23 than in the upper layer 22, which means that the liquid is more concentrated in the lower layer 23 than in the upper layer 22. The upper layer 22, having an open hole structure, is thus preferably located such that it resides nearest the skin of the user and the lower layer 23 facing the back sheet 30. Hereby, the liquid is rapidly guided into the spacer fabric and leaves a sense of dryness to the user.

The yarn in the layers 22, 23, 24 of the spacer fabric 20 is preferably made of thermoplastic fibers having low or negligible amount of absorption. Examples of such fibers are polyolefines, polyesters, polyamides or combinations thereof. Hereby, the liquid that enters the sanitary product 100 is spread at the surface of the fibers by wicking and not absorbed into the fibers. Wicking is the ability of a textile fiber to carry moisture along the surface of the fiber.

Preferably, the spacer fabric itself does not include any absorbing fibers, i.e. fibers made of absorbing materials. Instead, the spacer fabric may consist of thermoplastic fibers such as polyesters, polyamides or polyolefines.

On the contrary, for thermoplastic fibers, instead of the liquid being absorbed by the fiber, it sits in droplets on the fiber's surface and moves around by wicking. Thermoplastic fibers thus facilitate both washability and time for drying.

Absorption capacity is calculated by weight of absorbed liquid divided by the weight of the absorbing material defined at a certain time of exposure. In the sanitary industry, in addition to calculation of absorption capacity, liquid absorption is often measured by strike trough/penetration time, i.e. the speed at which liquid is absorbed by the product or by wetback (or rewet), i.e. the amount of liquid that is released by the product to the skin after absorption when pressure is applied to the product. In the case of the spacer fabric used in the invention, the spacer yarns prevent pressure to apply on the liquid retaining pad and therefore helps to lower the amount of wetback.

Figure 2A:
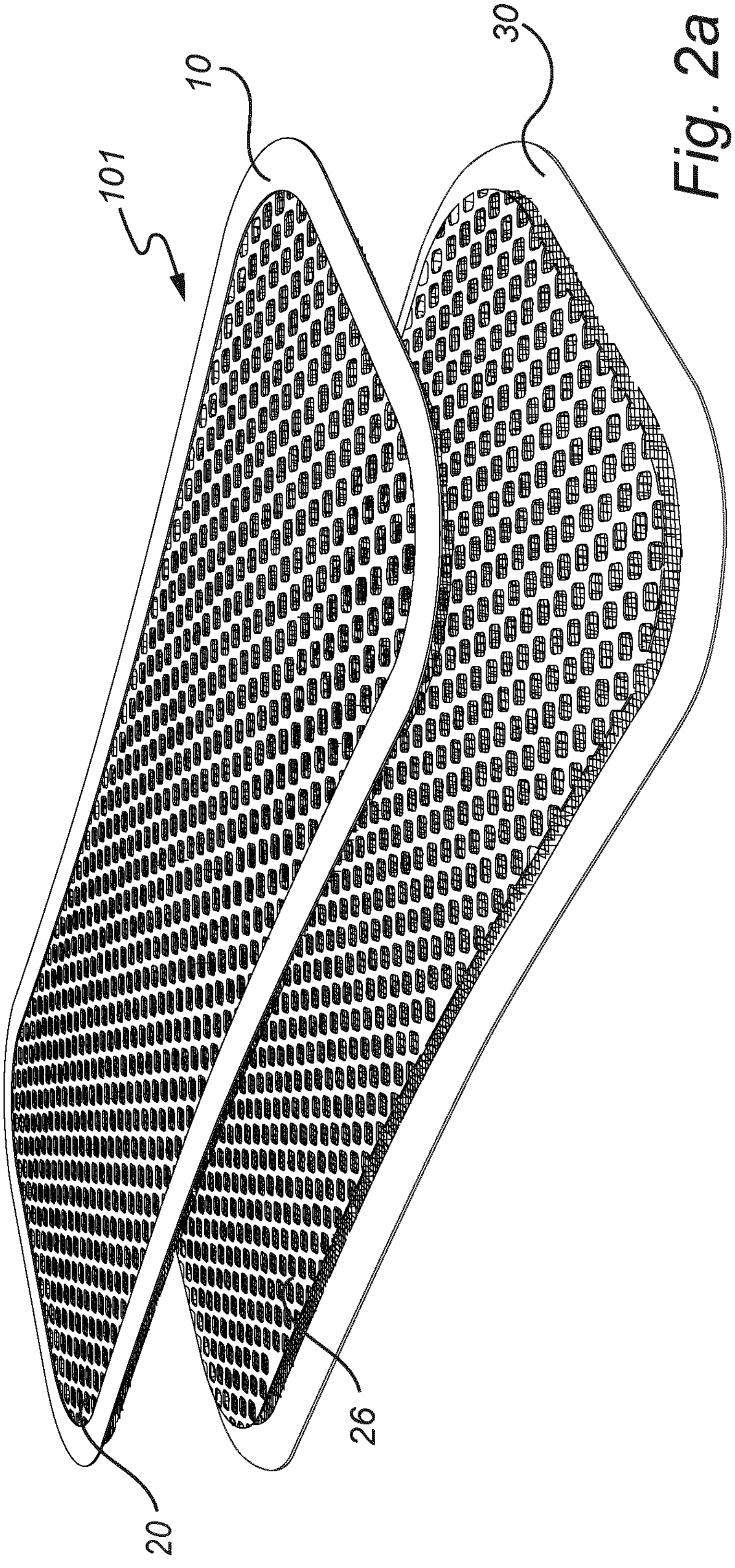
FIG. 2*a* illustrates, in an exploded view, a washable sanitary product according to a second embodiment of the invention, having two spacer fabric elements.
Figure 2B:
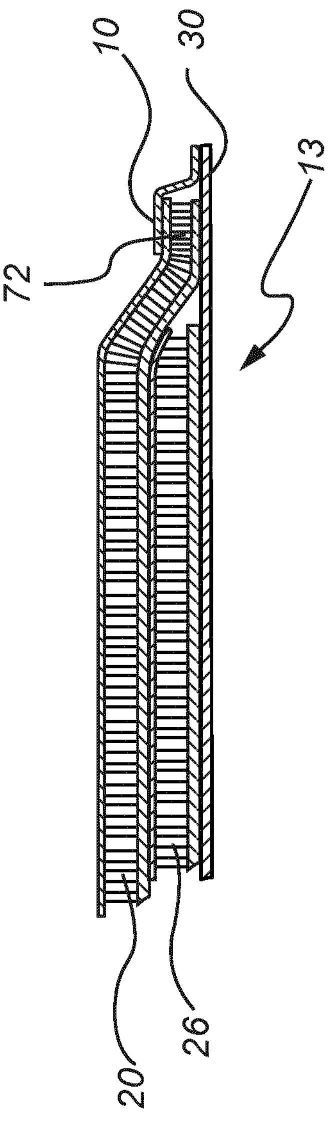
FIG. 2*b* is a cross section of the sanitary product of FIG. 2*a*.

FIG. 2*a-b* illustrate a sanitary product 101 having a liquid retaining pad 70 that consists of two elements of spacer fabric; an outer spacer fabric element 20 and an inner spacer fabric element 26. The outer spacer fabric 20 is located on top of the inner spacer fabric element 26 and is here slightly larger than the inner spacer fabric element, so that it extends beyond the outer edge of the inner element 26, as illustrated most clearly in FIG. 2*b*. This means that only the peripheral portion 72 of the outer spacer fabric element 20 is sandwiched between the annular liner 10 and the back sheet 30, thereby improving the functionality of the sealed container 13.

The outer and the inner spacer fabric 26 in FIG. 2*a-b* have the same thickness, e.g. about 3 mm respectively. However, it is also possible that the outer spacer fabric 20 is either thicker or thinner than the intermediate spacer fabric 24.

Similar to the outer spacer fabric element 20, also the inner spacer fabric element preferably has larger openings in its upper layer, so as to have lower flow resistance facing the user.

Figure 3A:
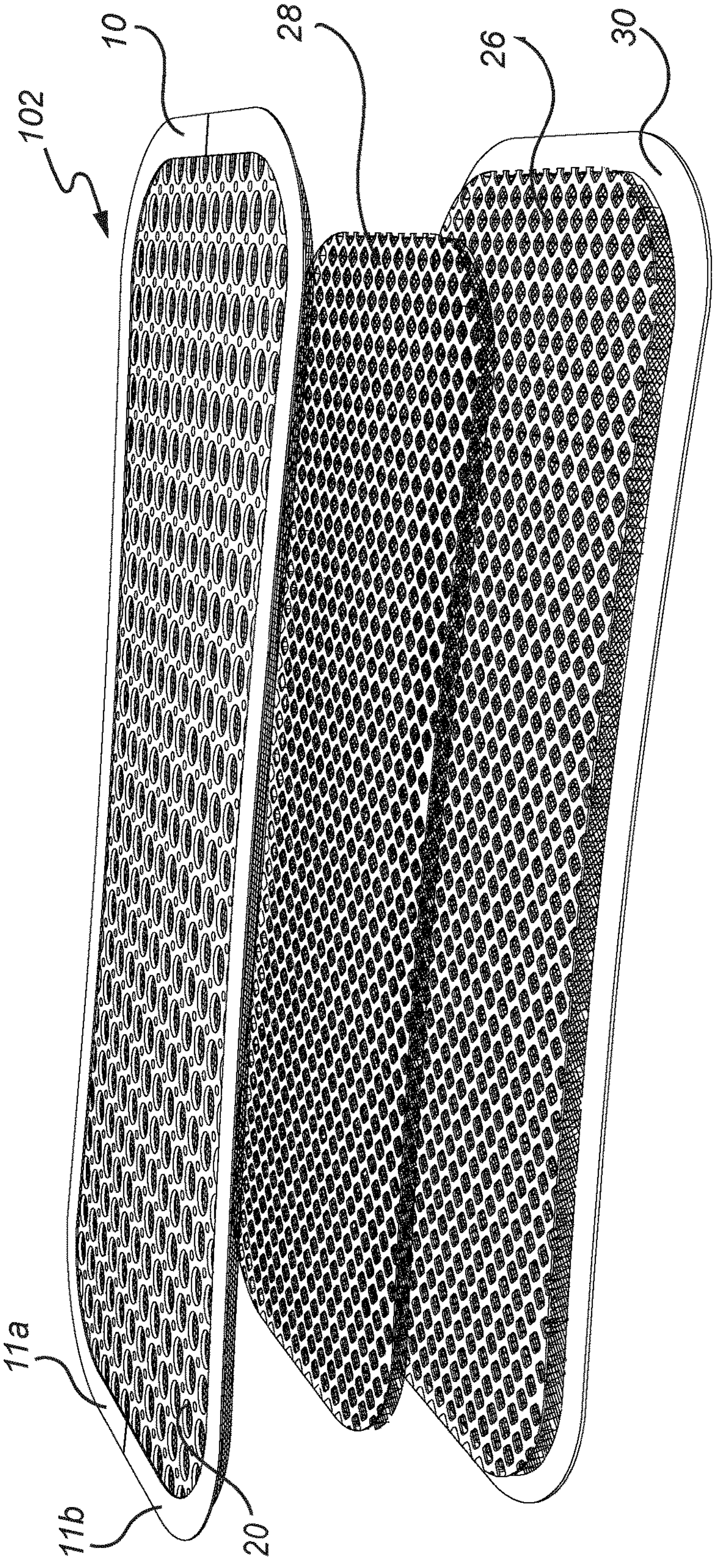
FIG. 3*a* illustrates, in an exploded view, a washable sanitary product according to a third embodiment of the invention, having three spacer fabric elements.
Figure 3B:
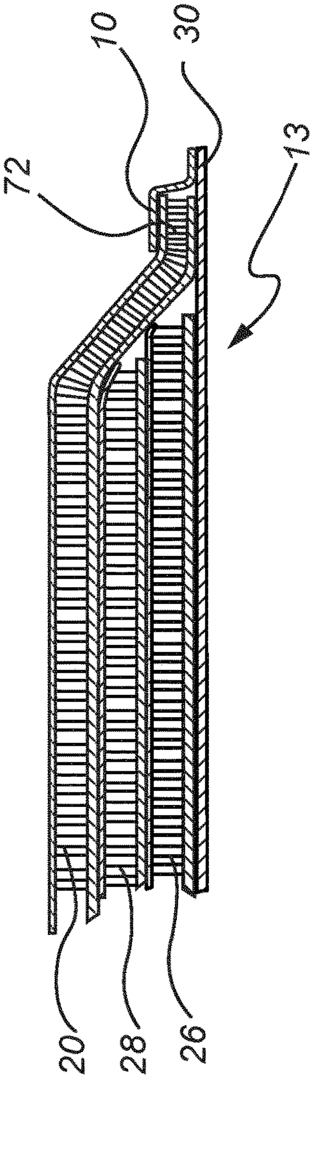
FIG. 3*b* is a cross section of the sanitary product of FIG. 3*a*.

FIG. 3*a-b* illustrate a sanitary product 102 having liquid retaining pad 70 that contains three elements of spacer fabrics; an outer spacer fabric 20, an inner spacer fabric 26, and an intermediate spacer fabric 28. Alternatively, the sanitary product 100 may include two or more intermediate spacer fabric elements 28 depending on the desired absorption capacity of sanitary product 100.

Similar to the product in FIG. 2*a*, the outer spacer fabric element 20 is slightly larger than the inner spacer fabric element 26, so that it extends beyond the outer edge of the inner element 26, as illustrated most clearly in FIG. 3*b*. This means that only the peripheral portion 72 of the outer spacer fabric element 20 is sandwiched between the annular liner 10 and the back sheet 30, thereby improving the functionality of the sealed container 13.

The size of the intermediate spacer fabric element(s) 28 may be even further reduced compared to the inner and outer spacer fabric elements 20, 26. This makes the liquid retaining pad 70 thicker in a central part than e.g. in the front and rear edges.

FIG. 3*a* illustrates that the outer spacer fabric 20 may be of a different material than the that of the intermediate spacer fabric 28 and the inner spacer fabric 26. The outer spacer fabric 20 here has bigger openings 25 in the upper layer than the two others. The bigger openings 25 have several advantages. It facilitates for the liquid pass into the liquid retaining pad 70 and makes the surface of the liquid retaining pad 70 feeling dry. It also promotes circulation of air between the user and the sanitary product 100. In addition, washing and drying is improved since water and air better can penetrate the liquid retaining pad 70. However, since the lower layer of the spacer fabric is adapted to collect more liquid than the upper layer, the lower layer of each spacer fabric element in the sanitary product 100 is advantageously equally dense with the same sizes of openings 25.

Figure 4:
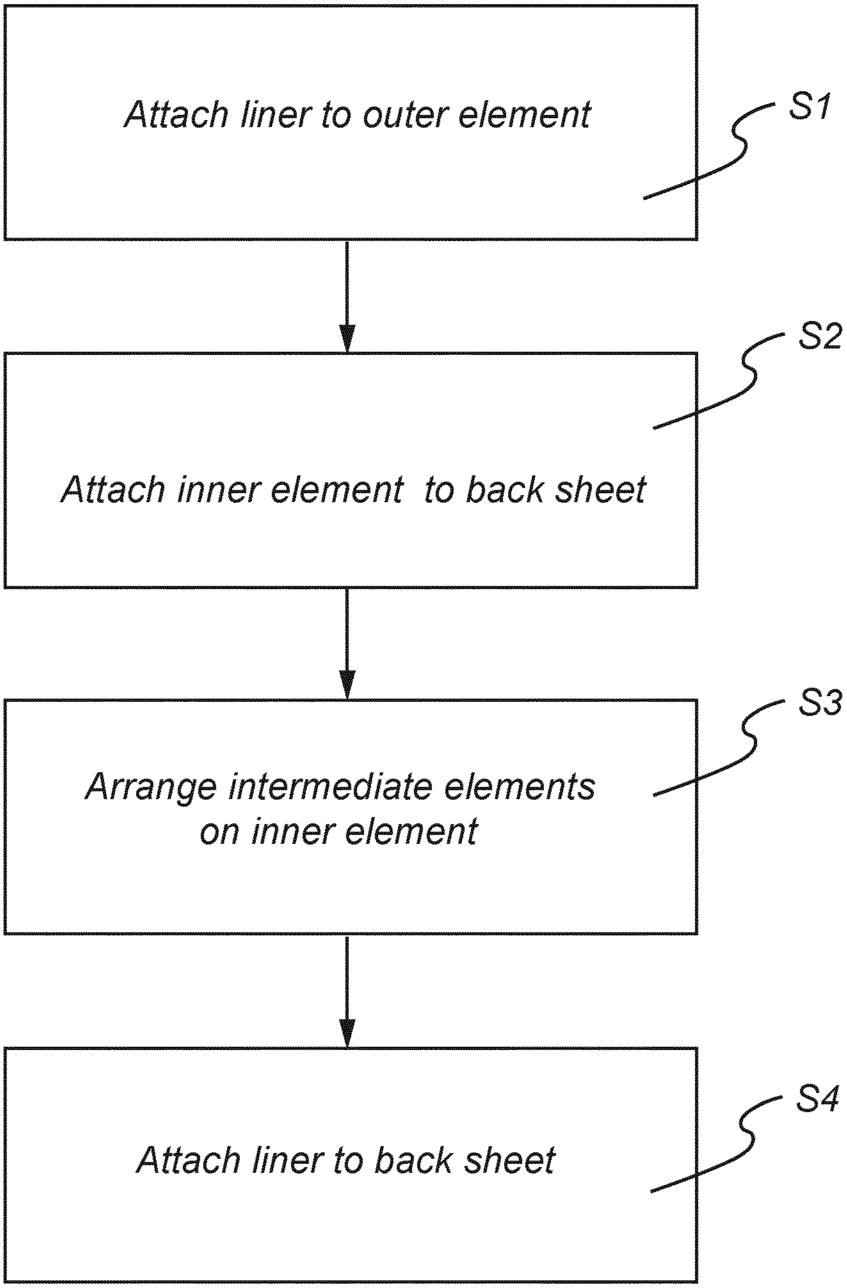
FIG. 4 illustrates a flow chart of a process for the manufacturing of the sanitary product in FIG. 3*a-b*.

FIG. 4 illustrates a flow chart for manufacturing of a sanitary product 100 as shown in FIG. 3*a*. First, in step S1, an annular liner 10 is attached to the outer spacer fabric element 20. To facilitate the process, the annular liner 10 may be separated into two sections 11*a*, 11*b*. Each section 11*a*, 11*b* of the annular liner 10 is attached to a perimeter 72 of the element 20 such that a portion of the annular liner 10 extends radially outside the element 20. The liner 10 may be attached by heat lamination, e.g. by applying pressure at a temperature between 130-150° C. for a duration of between 50-100 sec.

Then, in step S2, the inner spacer fabric element 26 is attached to the back sheet 30, again preferably by heat lamination. As illustrated in FIG. 3*a*, the thickness of the inner element 26 may be thicker than the outer element 20. For example, the inner element 26 maybe a few mm thicker, e.g. 5 mm instead of 3 mm. As a consequence of the pressure applied during step S2, the thickness of the inner element 26 in the finished product may be substantially the same as the outer element 20.

Then, in step S3, any intermediate spacer fabric elements 28 are arranged (not necessarily attached) on the inner element 26.

Finally, in step S4, the outer spacer fabric element 20, having the annular liner 10 attached thereto, is arranged on the stack of spacer fabric elements 26, 28, and the liner 10 is attached to the peripheral portion 32 of the back sheet 30.

By means of pressure and heat, applied only to the annular liner 10 and the portion 32 of the back sheet 30, a seam 15*b* is created between the annular liner 10 and the back sheet 30 with the peripheral portion 72 of the element 20 sandwiched in between.

Figure 5:
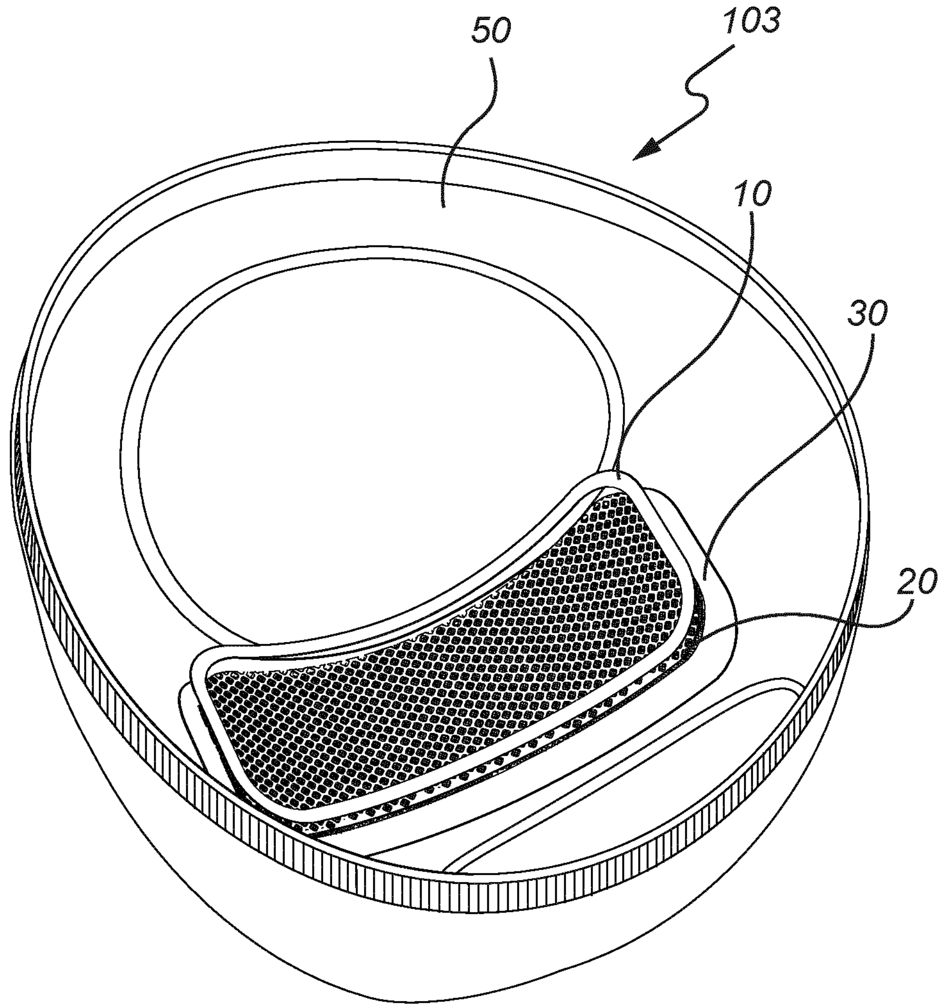
FIG. 5 illustrates, in an exploded view, a washable sanitary product that is integrated in an undergarment.

FIG. 5 illustrates a sanitary product 103 that is integrated in an undergarment 50. The sanitary product 100 in FIG. 5 is identical to the sanitary product 100 in FIG. 1 except from the difference that the back sheet 30 is attached to an undergarment 50 and not an underlaying layer. The back sheet can be attached to the undergarment by sewing or by glue.

The invention claimed is:

1. A washable sanitary product comprising:

a liquid impermeable back sheet, a liquid retaining pad, having an outer surface area adapted to reside nearest the skin of the user and an inner surface resting against the back sheet;

wherein a peripheral portion of the back sheet extends radially outside a peripheral portion of the liquid retaining pad;

wherein:

a liquid impermeable annular liner being sealingly attached to the outer surface of the liquid retaining pad along the peripheral portion of the liquid retaining pad by a first seal and to the peripheral portion of the back sheet by a second seal, such that the peripheral portion of the liquid retaining pad is sandwiched between the back sheet and the liner, the annular liner and the back sheet together form a liquid impermeable container for the liquid retaining pad, the liquid retaining pad comprises at least one element of spacer fabric that serves as both liquid distribution layer and as liquid retaining layer, and the first seal and the second seal both extend along the entire peripheral portion of the liquid retaining pad.

2. The washable sanitary product of claim 1, wherein the spacer fabric is a three-dimensional fabric made of an upper layer, a lower layer and an interconnecting layer of pile filaments that serve as spacer yarns.

3. The washable sanitary product of claim 2, wherein the upper layer has a lower flow resistance than the lower layer.

4. The washable sanitary product of claim 2 wherein the spacer fabric is a three-dimensional warp knit fabric.

5. The washable sanitary product of claim 1, wherein the spacer fabric element is located on the back sheet (30) without any intermediate liquid absorbing materials.

6. The washable sanitary product of claim 1, wherein the liquid retaining pad comprises an outer spacer fabric element, intended to be facing the skin of a user and at least one intermediate spacer fabric element sandwiched between the outer spacer fabric element and the back sheet.

7. The washable sanitary product of claim 1, wherein the at least one intermediate spacer fabric element has a smaller surface area than the surface area of the outer spacer fabric element and is located such that the outer spacer fabric element covers the at least one intermediate spacer fabric element.

8. The washable sanitary product of claim 1, wherein a spacer fabric element residing closest to the back sheet is attached to the back sheet.

9. The washable sanitary product of claim 1, further comprising an undergarment, wherein the back sheet, the liquid retaining pad and the annular liner are integrated in the undergarment.

10. A method for manufacturing a washable sanitary product, the method comprising:

providing a spacer fabric element, sealingly attaching a liquid impermeable annular liner to a peripheral portion of the spacer fabric element, along an entire peripheral portion of the liquid retaining pad, such that a radially extending portion of the annular liner extends radially outside the perimeter;

sealingly attaching the radially extending portion to a liquid impermeable back sheet, such that the perimeter of the spacer fabric element is sandwiched between the back sheet and the liner and so that the liquid impermeable annular liner is sealingly attached to the back sheet along the entire peripheral portion of the liquid retaining pad, wherein the annular liner and the back sheet together form a liquid impermeable container for the spacer fabric element.

11. The method of claim 10, wherein the annular liner is attached to the spacer fabric element and to the back sheet by means of heat lamination.

12. The method of claim 10, wherein the spacer fabric element is an outer spacer fabric element, further comprising:

providing an inner spacer fabric element, attaching the inner spacer fabric element to the back sheet before the step of sealingly attaching the radially extending portion of the annular liner to the back sheet.

13. The method of claim 12, further comprising:

providing at least one intermediate spacer fabric element on the inner spacer fabric element before the step of sealingly attaching the radially extending portion of the annular liner to the back sheet, such that the at least one intermediate spacer fabric element is sandwiched between the outer spacer fabric element and the inner spacer fabric element.

14. The method of claim 12, wherein the inner spacer fabric element is thicker than the outer spacer fabric element and/or the at least one intermediate spacer fabric element.

15. The method of claim 10, wherein the annular liner is provided as at least two sections and wherein the step of sealingly attaching the annular liner to the extending portion of the spacer fabric element comprises:

attaching a first annular liner section; and attaching a second annular liner section such that the first and second annular liner sections together form an annular liner.

* * * * *